__United States Patent__ [19]

Dattagupta

[11] Patent Number: 4,818,681

[45] Date of Patent: Apr. 4, 1989

[54] FAST AND SPECIFIC IMMOBILIZATION OF NUCLEIC ACIDS TO SOLID SUPPORTS

[75] Inventor: Nanibhushan Dattagupta, New Haven, Conn.

[73] Assignee: Molecular Diagnostics, Inc., West Haven, Conn.

[21] Appl. No.: 704,129

[22] Filed: Feb. 22, 1985

[51] Int. Cl.[4] ..................... C12Q 1/68; C07H 21/00; C12P 19/34
[52] U.S. Cl. .......................................... 435/6; 935/78; 536/27; 435/91; 436/94
[58] Field of Search ............... 435/6, 91; 436/94, 501; 935/78; 536/27

[56] References Cited

U.S. PATENT DOCUMENTS

| | | | |
|---|---|---|---|
| 4,282,352 | 8/1981 | Imahori et al. | 536/27 |
| 4,401,796 | 8/1983 | Itakura | 525/375 X |
| 4,419,444 | 12/1983 | Quash | 436/518 X |
| 4,472,572 | 9/1984 | Shizuya | 536/27 |
| 4,474,947 | 10/1984 | Hudson et al. | 536/27 |
| 4,474,948 | 10/1984 | Hudson et al. | 536/27 |
| 4,591,564 | 5/1986 | Watson | 435/6 X |

FOREIGN PATENT DOCUMENTS

| | | |
|---|---|---|
| 0070687 | 1/1983 | European Pat. Off. .......... 935/78 X |
| 0097805 | 1/1984 | European Pat. Off. . |
| WO/8403285 | 8/1984 | European Pat. Off. . |
| WO/8302277 | 7/1983 | PCT Int'l Appl. . |
| 8504674 | 10/1985 | PCT Int'l Appl. . |

OTHER PUBLICATIONS

Connor, B. J. et al *Proc. Natl. Acad. Sci. USA* vol. 80, 1983, pp. 278–282.
Maniatis, T. et al *Molecular Cloning A laboratory manual* Cold Spring Habor Laboratory, N.Y. 1982 p. 148.
Ashley, P. et al, *Anal. Biochem.* vol. 140, 1984, p. 93–103.
Deibel, M. R. et al, *Anal Biochem,* vol. 144, 1985, pp. 336–346.
Noyes, B. E. et al, *Cell,* vol. 5, No. 3, 1975, pp. 301–310.
Chemical Abstracts, vol. 95, 1981, p. 318, abstract No. 164568d, Columbus, OH, U.S.; N. F. Krynetskaya et al.: "Immobilized Tris(deoxyribonucleotides) Which are Primers for Enzymic Synthesis of Oligo- an Poly(deoxyribonucleotides)", & DOKL. AKAD. NAUK. SSSR 1981, 258(5), 1242–1245[Biochem.].

*Primary Examiner*—Charles F. Warren
*Assistant Examiner*—Jeremy Jay
*Attorney, Agent, or Firm*—Sprung Horn Kramer & Woods

[57] ABSTRACT

A process for synthesizing an oligonucleotide comprising linking a nucleoside phosphate to a solid support, through the heterocyclic moiety of the nucleoside, coupling a mono- or oligonucleotide to the nucleoside phosphate through its phosphate moiety, in at least one step enzymatically lengthening the mono- or oligonucleotide, cleaving the resultant oligonucleotide from the solid support-nucleoside phosphate at the phosphate moiety of the nucleoside, and separating the oligonucleotide. After cleaving and separating the solid support-nucleoside phosphate is recycled for further coupling. Advantageously the solid support-nucleoside phosphate is phosphorylated between separation and recycling.

3 Claims, No Drawings

FAST AND SPECIFIC IMMOBILIZATION OF NUCLEIC ACIDS TO SOLID SUPPORTS

Immobilization of nucleic acids to solid supports is essential for the separation and/or identification of specific genes. As has been discussed in application Ser. No. 511,063, filed July 5, 1983, now abandoned, which was refiled as application Ser. No. 815,694, filed Jan. 2, 1986, herein incorporated by reference, the step associated with the gel electrophoresis for the hybridization and detection of specific genomes can be eliminated by using a separation probe properly immobilized to a solid support. In application Ser. No. 511,064, filed July 5, 1983, now U.S. Pat. No. 4,542,102 issued July 5, 1983 and application Ser. No. 582,503, filed Feb. 22, 1984, now pending, herein incorporated by reference, we have described two methods of immobilizing nucleic acid probes to solid supports. The present invention is another method of immobilizing nucleic acids to solid supports. This method is superior to the other methods because of the specificity involved and the efficiency involved in the process. This method has several other advantages. For example, the method of the invention can be used to immobilize some primers which can be used to synthesize obligonucleotides on a solid support by using an enzyme represented in solid supports comprising cellulose, Sephadex, agarose, nylon, polystyrene, etc., in paper or bead form. This method eliminates the problem of purification, non-specific absorption, non-specific coupling and the problem of analysis. The invention can be described as follows.

A substrate for terminal deoxynucleotidyl transferase or an oligonucleotide will be immobilized to a solid support. The solid support should be such that it will not trap the probe and specifically it should have the porosity to exclude the separation probe and it should be nonreactive when the separation probe or the immobilized material has to be recovered from the reaction products. An adenosine triphosphate and related coenzyme immobilized matrix has been used for affinity chromatography of enzymes (U.S. Pat. Nos. 4,011,377 and 4,012,283). A similar reaction scheme can be used to immobilize other nucleic acid phosphates olignonucleotides, and the immobilized residues can be used for nucleic acid synthesis and probe immobilization of nucleic acid hybridization. UTP has also been immobilized by oxidatively reacting the sugar residue. G. Azzar et al, Anal. Biochem. 142, 518 (1984). The destruction of sugar residue makes it impossible to use this kind of support for the purpose where nucleoside phosphates are required for reaction.

The method can be used in several different ways. A typical example can be given in the following way: 5-allylamino UTP or 5-allylaminodeoxy UTP or 5-allylamino UDP or 5-allylaminodeoxy UDP or 8-hexylamino ATP or deoxy ATP can be coupled to a solid support via its $NH_2$ residues and then the residual nucleoside triphosphate immobilized onto the solid support will be used as a substrate for terminal deoxynucleotidyl transferase or polynucleotide phosphorylase to react with the 3' hydroxyl residue of a DNA or RNA, thus immobilizing the nucleic acid via a phosphordiester linkage to the immobilized nucleoside phosphates. The immobilized nucleoside phosphate can be immobilized in such a manner that the 3' hydroxyl or the 5' phosphate will be available for the enzyme. The nucleoside diphosphate or triphosphates can be part of a polynucleotide or oligonucleotide or a mononucleotide.

A purine nucleoside, which may be immobilized in accordance with the invention, has the following structural formula:

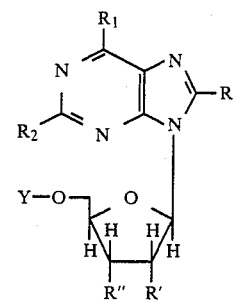

and a pyrimidine nucleoside, which may be immobilized in accordance with the invention, has the following structural formula:

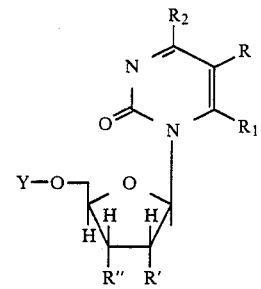

in which

R and $R_1$ each independently is —OH, —$NH_2$, —SH, —COOH or alkyl, allyl, aryl or alkenyl optionally substituted by —$NH_2$, —SH, —OH or

at least one of R and $R_1$ including an —$NH_2$, —SH, —OH or —COOH moiety, $R_2$ is —H, —$NH_2$ or —OH, Y is H or

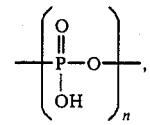

n is 1 to 3,

R' is H or OH, and

R" is H, OH or

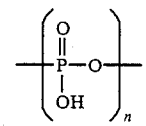

The immobilization can be done to a solid support via —S—S—,

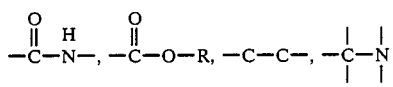

linkages using known reactions.

Chemical synthesis of deoxyoligonucleotides or ribonucleotides have been done in a method of stepwise addition of one residue to an immobilized nucleotide. The methods available are difficult and the purification and deprotection reactions produce many side products. The present method of utilization of solid phase enzymatic synthesis eliminates some of these problems and the probe can be used to label the nucleic acid before it is even removed from the solid support. The nucleic acid probe can also be used as a separation probe without removal from the support. An illustrative example is presented for the synthesis of oligoribonucleotide and oligodeoxyribonucleotide. The method utilizes an enzyme called $T_4$RNA ligase. Other enzymes which are primer independent, e.g., terminal nucleotidyl transferase can also be used with minor modification of the method.

The enzyme RNA ligase was first isolated by Silber et al, Proc.Natl.Acad.Sci., USA, 69, 3009 (1972) from $T_4$ phage infected *E. coli*. It catalyses a reaction between a 3' hydroxyl containing oligonucleotide and a 5' phosphorylated nucleotide (Snopeck et al, Biochem.Biophys.Res.Communication 68, 417 (1976)). It has been shown that 3'-, 5'-diphosphates of ribo- and deoxyribonucleosides also serve as donors in the presence of ATP. (England et al, Proc.Natl.Acad.Sci., USA., 74, 4839 (1977).) The principle of the synthesis can be described as follows:

Step 2: Addition of PNP

Step 3: Alkaline phosphatase treatment to dephosphorylate 3' hydroxyl residue.

Step 4: Repeat of 2 and 3 with the next nucleoside in sequence.

The example is a typical one. There are many variations of the reactions. In step 1 the immobilization of the acceptor olignonucleotide can be a deoxyribo- or ribonucleotide or their homopolymers or copolymers. The linkage can be through a modified nucleoside residue. The linkage can be single or multiple. The acceptor can be a highly polymerized or tri or tetramer (the minimum site of the acceptor for the enzyme system). The bond between the support can be

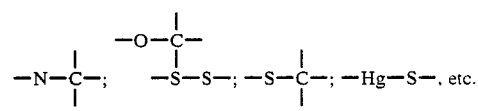

Step 1: Before immobilization reaction the proper initial acceptor is chosen such that 3'-hydroxyl will be available and coupling to solid support can be done under mild condition. Synthesis of the acceptor 5'-dU*pdApdApdApdApdA (U* is a 5-allylamino U residue) is done by a known phosphoramidite chemistry.

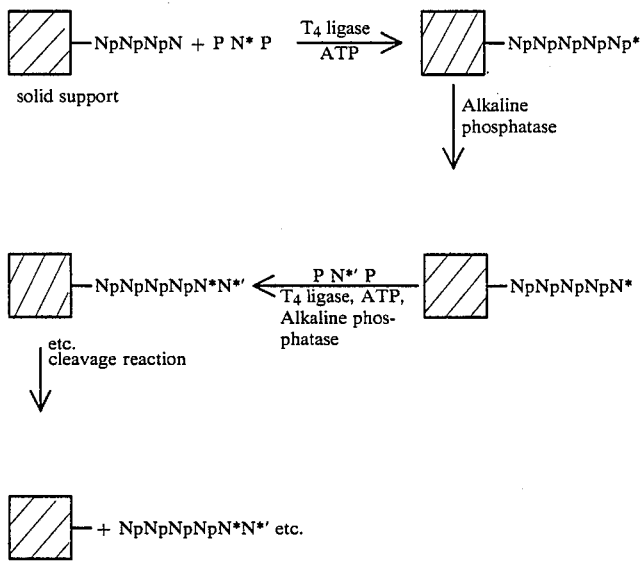

N — stands for nucleoside.

EXAMPLE I

Synthesis of a deoxyoligonucleotide specific for the detection of sickle cell anemia Step 1: Immobilization of an olignonucleotide acceptor with 3' hydroxyl available for reaction.

Using an Applied Biosystems Model 380A DNA synthesizer and their chemicals the pentanucleotide $(dA)_5$ is synthesized. In order to add d*U to $(dA)_5$ the compound 1 is synthesized. The synthesis scheme is as follows:

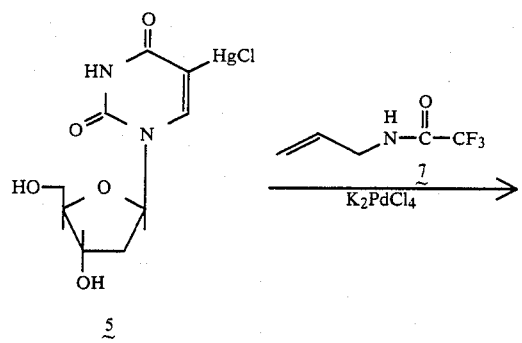
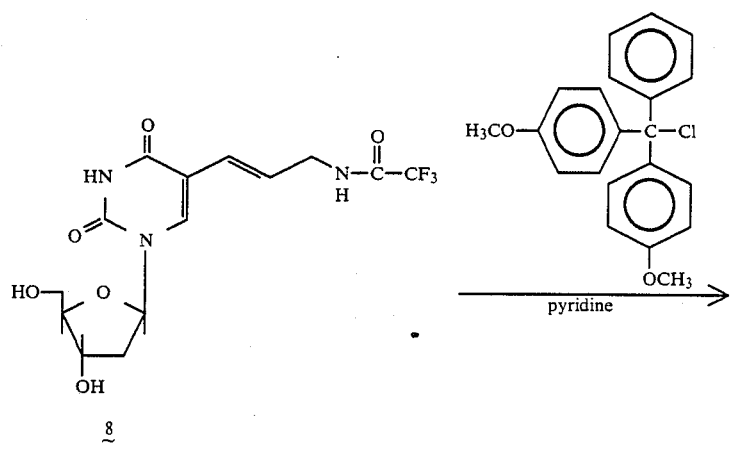
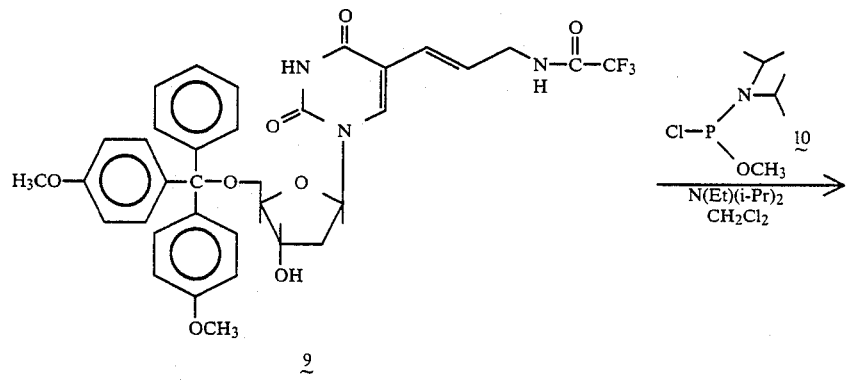
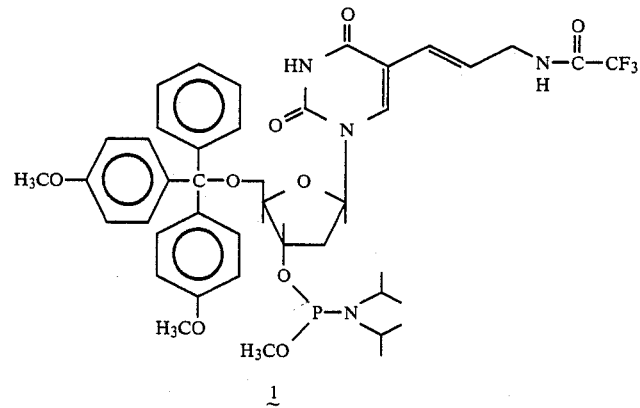

EXPERIMENTAL

In the following experimental discussion abbreviations are used as indicated:
g = gram
HPLC = high performance liquid chromtography
L = liter
mL = milliliter
M = molar
mM = millimolar
N = normal
eq = equivalents
mol = gram molecular formula (moles)
mmol = gram molecular formula $\times 10^{-3}$ (millimoles)
aq = aqueous
hr = hour Infrared (IR) spectra were obtained with a Perkin-Elmer Model 710B or 237 infrared spectrophotometer as solutions in CHCl$_3$ unless otherwise noted; the 1602 cm$^{-1}$ band of polystyrene film was used as an external calibration standard. Signals are reported as cm$^{-1}$.

Proton magnetic resonance ($^1$C NMR) spectra were obtained at 89.55 MHz using a Varian T-60 spectrometer; spectra were obtained in CDCl$_3$ solution unless otherwise noted. Chemical shifts are reported in parts per million downfield from the internal standard tetramethylsilane, unless otherwise noted.

Carbon-13 magnetic resonance ($^{13}$C NMR) spectra were obtained at 22.5 MHz using a JEOL FX90Q spectrometer with Fourier transform and with full proton broad-band noise decoupling; spectra were obtained in CDCl$_3$ solution unless otherwise noted. Carbon shifts are reported in parts per million downfield from the internal standard tetramethylsilane, unless otherwise noted.

Phosphorus-31 magnetic resonance ($^{31}$C PNMR) spectra were obtained at 36.21 MHz using a JEOL FX90Q spectrometer; spectra were obtained in CDCl$_3$ solution unless otherwise noted. Phosphorus shifts are reported in parts per million downfield from an external aqueous 15% H$_3$PO$_4$ standard.

Optical rotations were obtained on a Perkin-Elmer Model 141 Polarimeter.

Organic reagents were obtained from Aldrich Chemical Company and were used without purification, unless otherwise noted. Inorganic reagents were ACS reagent grade from Fisher Scientific Company or other major vendor. Reaction solvents were ACS reagent grade. Reagents used in oligonucleotide synthesis were obtained from Applied Biosystems, Inc. Brine refers to a saturated aqueous sodium chloride solution.

Thin layer chromtograph (TLC) was performed using silica gel 60F-254 plates from E. Merck. Column chromatography as performed using E. Merck Silica Gel 60 (70–230 mesh). All melting points reported are uncorrected.

5-Trifluoroacetamidoallyl-2'-deoxyuridine (compound 8)

A suspension of 5-chloromercuri-2'deoxyuridine (compound 5) (5.56 g; 12 mmol) in HPLC grade methanol (120 ml) was maintained under an inert gas atmosphere and treated at ambient temperature with 3-trifluoroacetamido-1-propene (7.33 g; 48 mmol; 4 eq) and K$_2$PdCl$_4$ (4.28.g; 1.1 eq). The reaction gradually becomes black and was allowed to stir for 22 hours. The mixture was treated with H$_2$S gas for several minutes then filtered through Celite, rinsed with MeOH and evaporated to dryness under reduced pressure from a 80° C. bath to give a crude semi-solid residue (7.0 g). The residue was chromatographed on a silica gel column developed with CH$_2$Cl$_2$/MeOH (5:1). The band which stained a blue color with modified p-anisaldehyde reagent and had an Rf=0.51 (CH$_3$CN)/MeOH 3:1) was collected and evaporated to dryness in vacuo to give a colorless foam. The product was crystallized from a minimum of methanol, filtered, washed with cold CHCl$_3$/MeOH (3:1) and vacuum dried. The mother liquor was worked for a second crop-total yield 1.01 g (22%). A recrystallization from MeOH afforded the title compound 8 as analytically pure tiny white needles with mp=183°-4° C. after drying in vacuo (<1.0 torr) at 64° C. overnight. IR (KBr) cm$^{-1}$ 3420, 3260, 1718, 1683 (br), 1560, 1478, 1283, 1190, 1102, 1061, 980, 788, 763, 737; $^1$HNMR (DMSO-d$^6$) (Ref. DMSO-d$^6$) δ 2.13 (d of d, J=6 Hz, 2H), 3.59 (br s, 2H). 3.70-3.97 (m, 3H), 4.25 (br s, 1H), 5.06 (br m, 1H), 5.20 (br m, 1H), 6.05-6.65 (m, 4H), 8.01 (s, 1H), 9.60 (br s, 1H); $^{13}$C NMR (DMSO-d$^6$) (Ref. DMSO-d$^6$) ppm 162.05, 155.29, 149.50, 138.05, 124.33, 124.14, 109.96, 87.53, 84.47, 70.23, 61.12, 39.93; [a]$_D$= +8.01° (c=0.87, MeOH).

Anal. Calcd. for C$_{14}$H$_{16}$N$_3$O$_6$F$_3$: C, 44.33; H, 4.25; N, 11.08. Found: C, 44.19; H, 4.10; N, 10.93.

5-Trifluoroacetamidoallyl-5'-0-(4,4'-dimethoxytrityl)-2'-deoxyuridine (compound 9)

A solution of compound 8 (0.60 g; 1.58 mmol) in anhydrous pyridine (8 ml) was maintained under an inert gas atmosphere and treated at ambient temperature with 4,4'dimethoxytrityl chloride (0.67 g; 1.25 eq). After stirring for 18 hours the reaction was poured into ice water (70 ml) with vigorous shaking. On standing ½ hour at 0° a gummy solid separates leaving a nearly clear solution which was decanted. The solid was washed once with H$_2$O (5 ml) then taken up in CH$_2$Cl$_2$ (10 ml), washed once with brine (5 ml) then the CH$_2$Cl$_2$ solution was dried over K$_2$CO$_3$, filtered and evaporated to dryness in vacuo to give a brownish foam. The crude product was purified by flash chromatography on a column of silica gel (Merck, Grade 60, 230-400 mesh, 60 A) (75 g) developed with 4.0% MeOH in CHCl$_3$ solvent (1.0 L). Fractions of ca. 20 ml. each were collected in tubes containing pyridine (10 μl) to inhibit deprotection of the 5'-hydroxyl. Fractions containing the major product band (RF=0.29; MeOH/CHCl$_3$ 7:93) were combined, filtered and evaporated to dryness in vacuo to give compound 9 (0.91 g; 85%) as a slightly yellowish foam. A fraction from the center of the elution band was freed of solvent, taken up in EtoAc, treated with Norit 211, filtered through Celite and evaporated to dryness under high vacuum (<1.0 torr) at 64° C. overnight to afford the analytical sample as a colorless foam with mp=105°-110° C. (dec.). IR (CHCl$_3$) cm$^{-1}$ 3370, 2920, 1715, 1695, 618, 1515, 1470, 1260, 1182, 1045, 842; $^1$H NMR (CDCl$_3$) δ 2.38 (br m, 2H), 3.25-3.75 (m, 5H), 3.75 (s, 6H), 4.40 (br m, 1H), 4.60 (br s, 1H), 5.39 (d, J=16 Hz, 1H), 6.10-6.55 (m, 2H), 6.70-6.95 (m, 5H), 7.15-7.45 (m, 10H), 7.84 (s, 1H; $^{13}$C NMR (CDCl$_3$) (Ref. CDCl$_3$) ppm 162.31, 158.74, 157.70, 156.01, 149.70, 144.04, 137.88, 135.65, 135.52, 130.12, 128.11, 127.26, 125.05, 113.48, 111.33, 86.94, 86.68, 85.25, 72.18, 63.60, 55.34, 42.66, 41.42.

Anal. Calcd. for C$_{25}$H$_{34}$N$_3$O$_8$F$_3$: C, 61.67; H, 5.03; N, 6.16. Found: C, 61.47; H, 5.19; N, 5.95.

5-Trifluoroacetamidoaminoallyl-5'-O-(4,4'-dimethoxytrityl)-2'-deoxyuridine-3'-O-(N,N-diisopropylaminomethoxy phosphine) (compound 1)

A solution of compound 9 (0.34 g; 0.5 mmol) in anhydrous CH$_2$Cl$_2$ (1.5 ml) maintained under an Argon atmosphere at ambient temperature was treated first with anhydrous diisopropylethylamine (0.35 ml; 0.259 g; 2 mmol; 4 eq) then dropwize, over 1 minute, with N,N-diisopropylaminomethoxy-chlorophosphine (compound 10) (0.19 ml; ca. 0.2 g; 2.2 eq). The resultant colorless solution is stirred for 20 minutes then transferred with EtOAc (20 ml) (EtOAc was previously washed with saturated aq NaHCO$_3$ then brine) to a separatory funnel, washed four times with brine (35 ml each), dried over Na$_2$SO$_4$, filtered and evaporated to dryness in vacuo to give a colorless glass (0.51 g). This crude product was taken up in anhydrous benzene (2 ml) and precipitated into rapidly stirred anhydrous pentane (60 ml) at $-78°$ C. under an Argon atmosphere. The resulting suspension was filtered, washed with $-78°$ C. pentane and vacuum dried at $<1$ torr over KOH overnight to obtain the title compound 1 (0.38 g; 93%) as a white amorphous powder. IR (CHCl$_3$) cm$^{-1}$ 2965, 1722, 1698, 1618, 1518, 1470, 1262, 1185, 1045, 988, 842; $^1$H NMR (CD$_2$Cl$_2$) δ 0.95-1.30 (m, 12H), 2.20-2.60 (m, 2H), 3.24 and 3.37 (d od d, J=13 Hz, 3H) (P—O—CH$_3$), 3.20-3.80 (m, 6H), 3.75 (s, 6H), 4.17 (br m, 1H), 4.68 (v br m, 1H), 5.42 (d, J=16 Hz, 1H), 6.15-6.55 (m, 3H), 6.75-6.95 (m, 4H), 7.20-7.50 (m, 10H), 7.79 (s, 1H); $^{13}$C NMR (CD$_2$Cl$_2$) (Ref. CD$_2$Cl$_2$) ppm 162.40, 159.21, 157.78, 149.78, 144.71, 138.34, 136.00, 130.53, 128.71, 128.45, 127.54, 125.66, 125.27, 113.82, 111.48, 87.23, 86.31, 85.60, 55.75, 43.78, 43.20, 42.94, 24.99, 24.60; $^{31}$PNMR (CD$_2$Cl$_2$) ppm 149.30, 148.87, 14.11 (ca. 12% impurity) 8.18 (ca. 4% impurity).

Attachment of Compound 1 to Oligonucleotides

The 5 unit oligonucleotides dA—p—dA—p—dA—p—dA—p—dA are synthesized using an Applied Biosystems Model 380A DNA Synthesizer on control pore glass solid support. Immediately prior to attaching compound 1 to the 5' end of the oligomer, the 5'-0-(4,4'-dimethoxytrityl) protecting group is cleaved on the machine with 3% CCl$_3$CO$_2$H in CH$_2$Cl$_2$ for 90 seconds. The support-bound 5'-deprotected oligomer was washed with CH$_2$CN and dried in an Argon stream. Subsequent steps were performed without the machine, but using the same chemistry;

1. The support-bound oligomer was removed from the container (column) used for automated synthesis and transferred to a dry septum-cap vial under an Argon atmosphere.
2. The bound oligomer was treated with a 20–30 fold excess of 0.5M 1H-Tetrazole in anhydrous CH$_3$CN followed immediately with a similar excess of compound 1 in CH$_3$CN. Incubate 30 minutes with gentle agitation.
3. Pipette off reagents and wash bound oligomer with 3 portions of CH$_3$CN.
4. Treat with an excess of I$_2$—H$_2$O-Lutidine—THF (0.1M: 1:10:40) and agitate for 15 minutes.
5. Pipette off reagent and wash bound oligomer with 4 portions of CH$_3$CN.
6. Treat with an excess of Thiophenol-triethylamine-dioxane for 60 minutes.
7. Pipette off reagent and wash the bound oligomer with 4 portions of MeOH.
8. Treat with conc. aq. NH$_4$OH for 2 hours at ambient temperature. (Removes protected oligonucleotide from the support).
9. Add more conc. aq. NH$_4$OH and heat at 50° C. overnight. (Removes all protecting groups except the dimethoxytrityl).

The synthesized oligonucleotide was detritylated with 3% CCl$_3$CO$_2$H in CH$_2$Cl$_2$ then purified by electrophoresis on polyacrylamide gel and used to react with an activated support.

This synthesized oligonucleotide has an —NH$_2$ residue which can be easily coupled to any activated solid support. N-hydroxysuccinimide ester of agarose is prepared according to the method described by Cuatrecasas and Parikh, Biochemistry, 11, 2291 (1972). About 1 gm of moist activated agarose is shaken gently in 5 ml 0.1M NaHCO$_3$ buffer (pH 8.6) for 10 minutes at 4° C. Then the oligonucleotide 1 mg/ml in NaHCO$_3$ buffer is added. The reaction is allowed to proceed for 4 hours at 4° C. with gentle shaking of the solution. Then the unreacted residues are blocked by adding 1M glycine in the same buffer. The gel is washed thoroughly with NaHCO$_3$ buffer (pH 8.6) then with 50 mM HEPES (pH 8.3). After this washing, the agarose with the immobilized acceptor is ready for the next step.

Step 2: Addition of pNp:

In order to produce an easily dissociable bond between the acceptor and the product, the first 2-3 residues used are ribonucleotides. After that deoxyribonucleotide residues are added. The procedure is identical in both cases. Only one step addition is described below. The reaction mixture containing ~300 μl immobilized acceptor (step 1)

300 μMoles pNp or deoxy pNp purchased from P.L. Biochemicals 10 ug Bovine serum albumin 100 units of T$_4$ RNA ligase (P.L. Biochemistry) in 1 ml total volume of a buffer mixture containing 50 mM HEPES (pH 8.3); 20 mM MgCl$_2$; 3.3 mM dithiothreitol; 8% (v/v) glycerol and 600 μMoles of ATP. The mixture is incubated for 1 hour at 37° C. After the reaction the mixture is washed and the solid is separated for the next step. The solution can be reused for coupling the identical nucleoside.

Step 3: The resin from step 2 is washed and resuspended in HEPES buffer (pH 8.3), then treated with 50 units of alkaline phosphatase (International Biotechnologies Inc.) at 37° C. for 2 hours and then washed with HEPES buffer.

Step 4: After the dephosphorylation step of 3, the immobilized residue is ready for the repeat of the cycle of step 2 and 3 After the desired synthesis, the oligonucleotide can be removed from the support if a labile residue is provided, e.g., if the first two residues in step 2 are ribonucleotide residues and the rest is deoxy residue, digestion with sodium hydroxide should cleave the phosphodiester linkage at that site. If an oligoribonucleotide is used in step 1, linkage can be disrupted at that site in a similar manner or digestion with a ribonuclease can be used. If RNA synthesis is done, deoxyribose acceptor can be immobilized and can be cleaved with DNase after the synthesis.

Finally the product is sequenced to establish the efficiency and specificity of the process.

Following this procedure, an oligonucleotide with 20 residues long is synthesized and labeled while on the support, by using $^{32}P$ labeled PCP (from New England Nuclear) the tested for its ability to detect sickle cell defect by a hybridization technique as has been described by Conner et al (Proc.Natl.Acad.Sci., USA, 80, 278 (1983)). The sequence prepared has two ribonucleotide residues and 1% deoxyribonucleotide residues.

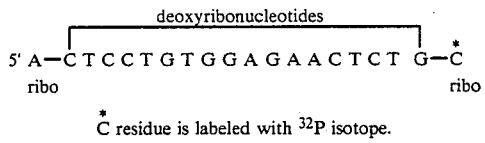

$\overset{*}{C}$ residue is labeled with $^{32}P$ isotope.

Many other oligonucleotides can be synthesized in an identical fashion.

EXAMPLE 2

Immobilization of separation probe for sickle cell anemia detection via TdT reaction About 1 mg of CNBr activated Sepharose Cl-4B (prepared by conventional manner) is washed with 1 mM HCl. 5-allylamino dUTP prepared according to Lager et. al. Proc. Natl. Acad. Sci, U.S.A. 78, 6633 (1981) is dissolved in water (concn 1 mg/ml) and kept frozen. After the solid support activated with cyanogenbromide is washed with HCl they are kept submersed under 0.1M $NaHCO_3$ (pH 8.3) for 30 minutes. The buffer is then washed and fresh solution of $NaHCO_3$ is added. The washing process is repeated for 3 times. Then the support is allowed to settle by gravity and the buffer is removed. Once the solid cake is formed 5-allylamino dUTP is added ~10 ml of dUTP solution to 1 ml of the solid, followed by 5 ml $NaHCO_3$ buffer. The mixture is shaken by hand and gently shaken in the cold room for 16 hours. After this time the support is washed to remove the unreacted AAdUTP. Then $3\times 2$ ml 0.2M glycerine solution is added to block other unreacted active site. The solid is then finally washed with TdT buffer (0.2M—K-cacodylate buffer (pH 7.2).

The probe which is immobilized is prepared by digestion of a plasmid pSS737 or $\beta$ pbr322 pst. These plasmids have a pstI segment of human DNA that includes $\beta$-hemoglobin gene. It is easily prepared by published procedure (obtained from Dr. J. Wilson, Medical College of Georgia Research Institute and published in Geever et al., Proc. Natl. Acad. Sci., U.S.A., 5081 (1981). One sample of the plasmid pSS737 is digested to completion with DdeI; another sample is digested with Hinf I. The resulting DNA segments are separated according to size by electrophoresis in a preparative, low melting temperature agarose gel. The gel is stained with ethidium bromide for visualization and DNA bands 0.34 Kb from the HinfI digest and 0.20 Kb from DdeI digest are excised. 0.34 Kg fragment is immobilized and 0.20 Kb fragment is labeled with 32p by using a polynucleotide kinase.

100–200 $\mu l$ of the solid with immobilized A-UTP is suspended in 200 mM cacodylate buffer and 100 $\mu g$ of the separation probe, 0.34 Kb. HinfI segment of pSS 737, application Ser. No. 511,063, supra, in the same buffer are mixed in an Eppendorf tube. To this $MgCl_2$ (final conc 4 mM); 1 mM dithiothreitol and 10 units of TdT from BRL are added, the mixture is incubated at 37° C. for 16 hours. Then the support is washed with cacodylate buffer.

In order to estimate the capacity of such a supporting material, calf thymus DNA is used. Using $^{32}P$ labeled or $^{125}I$ labeled DNA it is possible to estimate the maximum capacity of the support.

As the hybridization procedure involves single-stranded DNAs, the solid support upon which the selector probe is immobilized must be pretreated so that the unknown DNA and the detector probe do not bind to it indiscriminately. The pretreatment is done with a solution known as Denhardt's solution (0.2% each of bovine serum albumin, ficoll and polyvinylpyrrolidone in water), in which, along with some salt and buffer (e.g., $6\times$SSC, 0.1M Tris, pH 8), the solid is suspended for a few hours at the temperature to be used for hybridization (e.g., 65° C.). This solution is then replaced with hybridization medium that includes denatured sample (unknown) DNA from a patient and denatured detector probe, and DNA annealing is allowed to proceed for a few hours. Two representative hybridization conditions are: (i) $6\times$SSC, 0.1M Tris, pH 8, 65° C., the inclusion of Denhardt's solution being optional; (ii) $4\times$SSC, 40% formamide, 40° C., ±Denhardt's solution.

After hybridization, DNAs that have not been faithfully base paired to the selector probe are washed from the support by a series of solutions that demand extensive annealing for hybrid stability to be maintained. For example, the solid particles are washed with a large volume of $0.2\times$SSC at 65° C. (at which low salt concentration poorly base paired hybrids will dissociate), then it is washed with a large volume of $0.2\times$SSC at room temperature. The particles then are air dried. If the detector probe is labeled with 32P, the particles are counted in a scintillation counter. Alternatively, autoradiographic detection can be done. The extent of radioactivity associated with the particle is an indication of the disease, sickle cell anemia.

It will be understood that the specification and examples are illustrative but not limitative of the present invention and that other embodiments within the spirit and scope of the invention will suggest themselves to those skilled in the art.

What is claimed:

1. A process for immobilization of a nucleic acid comprising
   (a) linking a nucleoside phosphate to a solid support through the nitrogen heterocyclic moiety of the nucleoside phosphate and
   (b) enzymatically covalently coupling a nucleic acid to the resultant immobilized nucleoside phosphate from step (a) via a phosphate or linkage.

2. A process according to claim 1, wherein the nucleic acid is a sickle cell anemia nucleic acid probe.

3. A process according to claim 1, wherein the enzymatic coupling is conducted in the presence of an enzyme, wherein the enzyme is terminal deoxynucleotidyl transferase.

* * * * *

UNITED STATES PATENT AND TRADEMARK OFFICE
CERTIFICATE OF CORRECTION

PATENT NO. : 4,818,681
DATED : April 4, 1989
INVENTOR(S) : Nanibhushan Dattagupta It is certified that error appears in the above-identified patent and that said Letters Patent is hereby corrected as shown below:

| | |
|---|---|
| Col. 1, line 64 | Correct spelling of --phosphodiester-- |
| Col. 7, line 52 | Correct spelling of --chromatograph-- |
| Col. 8, line 58 | Delete "618" and substitute --1618-- |
| Col. 8, line 60 | Delete "4.40" and substitute --4.10- |
| Col. 8, line 67 | Delete "$C_{25}$" and substitute --$C_{35}$-- |
| Col. 9, line 27 | Delete "d od d" and substitute --d of d-- |
| Col. 11, line 10 | After "A A" delete "C" and substitute --G-- |
| Col. 11, line 28 | Delete "M" and substitute --$\underline{M}$-- |
| Col. 11, line 38 | Delete "M" and substitute --$\overline{\overline{M}}$-- |
| Col. 11, line 55 | Delete "Kg" and substitute --$\overline{\overline{K}}$b-- |
| Col. 12, line 55 | Delete "phosphate or" and substitute --phosphodiester-- |

Signed and Sealed this

Twenty-ninth Day of May, 1990

*Attest:*

HARRY F. MANBECK, JR.

*Attesting Officer*  *Commissioner of Patents and Trademarks*